United States Patent
Meijer et al.

(10) Patent No.: US 10,561,661 B2
(45) Date of Patent: Feb. 18, 2020

(54) PURINE DERIVATIVE COMPOUNDS FOR MEDICAL USE

(71) Applicants: MANROS THERAPEUTICS, Roscoff (FR); UNIVERSITY OF CHICAGO, Chicago, IL (US)

(72) Inventors: Laurent Meijer, Roscoff (FR); Nassima Oumata, Roscoff (FR); Hervé Galons, Paris (FR); Aida Gabdoulkhakova, Chicago, IL (US); Vladimir Riazanski, Clarendon Hills, IL (US); Deborah Nelson, Riverside, IL (US)

(73) Assignees: MANROS THERAPEUTICS, Roscoff (FR); UNIVERSITY OF CHICAGO, Chicago, IL (US)

( * ) Notice: Subject to any disclaimer, the term of this patent is extended or adjusted under 35 U.S.C. 154(b) by 13 days.

(21) Appl. No.: 14/623,799

(22) Filed: Feb. 17, 2015

(65) Prior Publication Data
US 2015/0320753 A1 Nov. 12, 2015

(30) Foreign Application Priority Data
Feb. 17, 2014 (EP) .................................. 14 305215

(51) Int. Cl.
| | | |
|---|---|---|
| A61K 31/52 | (2006.01) | |
| C07D 473/16 | (2006.01) | |
| G01N 33/50 | (2006.01) | |
| A61K 45/06 | (2006.01) | |

(52) U.S. Cl.
CPC .............. *A61K 31/52* (2013.01); *A61K 45/06* (2013.01); *G01N 33/5091* (2013.01)

(58) Field of Classification Search
CPC ............................. A61K 31/52; C07D 473/16
See application file for complete search history.

(56) References Cited

FOREIGN PATENT DOCUMENTS

| EP | 2907514 A1 * | 8/2015 | ............. A61K 31/52 |
|---|---|---|---|
| WO | 97/20842 A1 | 6/1997 | |
| WO | 2004/016612 A2 | 2/2004 | |
| WO | WO-2004016612 A2 * | 2/2004 | ............. A61K 31/52 |
| WO | 2006/042949 A1 | 4/2006 | |

OTHER PUBLICATIONS

Cheson, B.D., et al. "Neurotoxicity of purine analogs: a review." J. Clin. Oncology. (1994), vol. 12, pp. 2216-2228.*
Lee, K., et al. "Macrophage Function Disorders." (c) Sep. 2013. John Wiley & Sons, Ltd. Available from: < http://onlinelibrary.wiley.com/doi/10.1002/9780470015902.a0002174.pub3/full >.*
Ordway, D., et al. "Clinical Concentrations of Thioridazine Kill Intracellular MultiDrug-Resistant Mycobacterium tuberculosis." Antimicrobial Agents and Chemotherapy. (Mar. 2003), pp. 917-922.*
Estrella, J.L., et al. "A novel in vitro human macrophage model to study the persistence of Mycobacterium tuberculosis using vitamin D3 and retinoic acid activated THP-1 macrophages." Frontiers in Microbiology: Cellular and Infection Microbiology. (Apr. 18, 2011), vol. 2, Article 67, pp. 1-16.*
Harbeck, R., et al. "MiniReviews—Immunophenotyping of Bronchoalveolar Lavage Lymphocytes." Clinical and Diagnostic Laboratory Immunology. (May 1998), vol. 5, No. 3, pp. 271-277.*
MedicineNet. "Cystic Fibrosis." © Mar. 7, 2009. Accessed Jul. 21, 2018. Available from: < https://www.medicinenet.com/cystic_fibrosis/article.htm#what_is_cystic_fibrosis >. (Year: 2009).*
American Academy of Allergy Asthma and Immunology. "Asthma Symptoms, Diagnosis, Management, and Treatment." © Aug. 2, 2011. Accessed Jul. 21, 2018. Available from: < https://www.aaaai.org/conditions-and-treatments/asthma >. (Year: 2011).*
Cafasso, J. "Pseudomonas Infections." © Jul. 9, 2013. Accessed Jul. 21, 2018. Available from: < https://web.archive.org/web/20130709004659/https://www.healthline.com/health/pseudomonas-infections >. (Year: 2013).*
Antimicrobe. "Actinomyces species (Actinomycoses)." © 2002. Accessed Jul. 21, 2018. Available from: < http://www.antimicrobe.org/b73.asp >. (Year: 2002).*

(Continued)

*Primary Examiner* — Andrew D Kosar
*Assistant Examiner* — John S Kenyon
(74) *Attorney, Agent, or Firm* — Oliff PLC

(57) ABSTRACT

A method for treatment of disease by reduction in macrophages-mediated bacterial killing, including administration to patients in need a compound of formula (I):

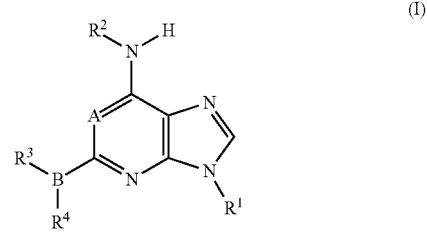

Figure 1A:
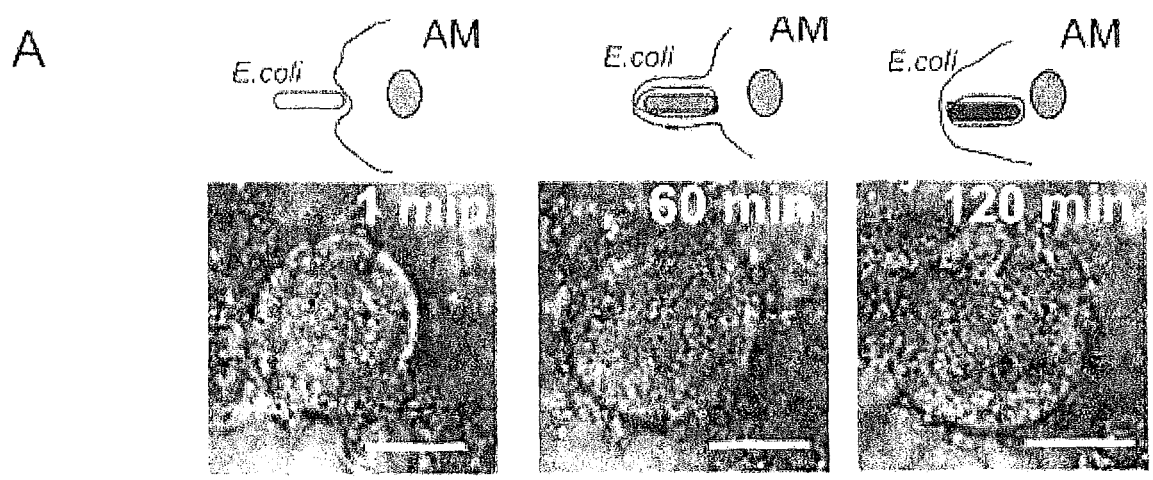

wherein A is N or CH; B is NO, or S; $R^1$ is H, $(C_1-C_4)$alkyl group, methyl$(C_1-C_6)$cycloalkyl group or $(C_1-C_6)$cycloalkyl group; $R^2$ is an aryl, arylmethyl group or methylheteroaryl group as methylpyridine and methylthiophene; $R^3$ is absent when B is O or S, or is H or $(C_1-C_4)$alkyl group when B is N; $R^4$ is $(C_1-C_5)$alkyl group or $(C_1-C_4)$cycloalkyl group, groups bearing a carboxylic acid group, and $(C_1-C_5)$alkyl group or $(C_1-C_4)$cycloalkyl substituted by hydroxyl group, halogen group or methoxy group, when B is N, $R^3$ and $R^4$ can together form a 5- or 6-membered heterocycle substituted by carboxylic acid group, substituted by a halogen atom, hydroxyl group, methoxy group or hydroxymethyl group, or pharmaceutically acceptable salt. Also provided are new compounds relating to this use.

20 Claims, 6 Drawing Sheets

(56) References Cited

OTHER PUBLICATIONS

Ordway, D., et al. "Clinical Concentrations of Thioridazine Kill Intracellular MultiDrug-Resistant Mycobacterium tuberculosis." Antimicrobial Agents and Chemotherapy. (Mar. 2003), pp. 917-922. (Year: 2003).*

Estrella, J.L., et al. "A novel in vitro human macrophage model to study the persistence of Mycobacterium tuberculosis using vitamin D3 and retinoic acid activated THP-1 macrophages." Frontiers in Microbiology: Cellular and Infection Microbiology. ( Apr. 18, 2011), vol. 2, Article 67, pp. 1-16. (Year: 2011).*

Porto, P., et al. "Dysfunctional CFTR Alters the Bactericidal Activity of Human Macrophages against Pseudomonas aeruginosa." (May 18, 2011). PLoS One. 6(5): e19970. (Year: 2011).*

Harbeck, R., et al. "MiniReviews—Immunophenotyping of Bronchoalveolar Lavage Lymphocytes." Clinical and Diagnostic Laboratory Immunology. (May 1998), vol. 5, No. 3, pp. 271-277. (Year: 1998).*

Anke Di. et al., "CFTR regulates phagosome acidification in macrophages and alters bactericidal activity," Nature Cell Biology, 2006, vol. 8, No. 9, pp. 933-944.

Ludmila V. Deriy et al., "Disease-causing Mutations in the Cystic Fibrosis Transmembrane Conductance Regulator Determine the Functional Responses of Alveolar Macrophages," The Journal of Biological Chemistry, 2009, vol. 284, No. 51, pp. 35926-35938.

Marine Henry et al., "Prediction in Vivo Efficacy of Therapeutic Bacteriophages Used To Treat Pulmonary Infections," Antimicrobial Agents in Chemotherapy, 2013, vol. 57, No. 12, pp. 5961-5968.

David J. Hackam et al., "Regulation of Phagosomal Acidification," The Journal of Biological Chemistry, 1997, vol. 272, No. 47, pp. 29810-29820.

Anna M. van Heeckeren et al., "Role of Cftr genotype in the response to chronic Pseudomonas aeruginosa lung infection in mice," Am J Physiol Lung Cell Mol Physiol, 2004, vol. 287, pp. L944-L952.

Nassima Oumata et al., "Practical Synthesis of Roscovitine and CR8," Organic Process Research & Development, 2009, vol. 13, No. 3, pp. 641-644.

C.J. Cooper et al., "Stability and purity of a bacteriophage cocktail preparation for nebulizer delivery," Letters in Applied Microbiology, 2013, vol. 58, pp. 118-122.

Deborah J. Nelson et al., "Immunoglobulin G-induced Single Ionic Channels in Human Alveolar Macrophage Membranes," J. Clin. Invest., 1985, vol. 76, pp. 500-507.

Debebe Alemayehu et al., "Bacteriophages MR299-2 and NH-4 Can Eliminate Pseudomonas aeruginosa in the Murine Lung and on Cystic Fibrosis Lung Airway Cells," mBio, 2012, vol. 3, No. 2, pp. 1-9.

* cited by examiner

PURINE DERIVATIVE COMPOUNDS FOR MEDICAL USE

FIELD OF THE INVENTION

The present invention relates to purine derivative compounds and substituted imidazo[4,5-b]pyridines derivatives for their use for treating a disease characterized by a reduction in macrophage-mediated bacterial killing, in particular alveolar macrophages (AMs), and more particularly a disease resulting from impaired acidification of phago-lysosomes in macrophages, in particular alveolar macrophages.

More particularly, the invention relies upon said derivatives, for their use for the treatment of cystic fibrosis (CF) and more generally for the treatment of diseases involving pulmonary microbial infections and even more broadly for their use in the treatment of pulmonary infectious diseases.

BACKGROUND OF THE INVENTION

Cystic fibrosis, the most common lethal autosomal recessive inherited disease, is linked to non-functional chloride channel CFTR (for Cystic Fibrosis Trans-membrane Conductance Regulator).

Deletion of phenylalanine 508 (Δ508F CFTR) in the CFTR protein encoding gene accounts for the most prevalent mutation in cystic fibrosis patients and represents almost 70% of the mutations. Δ508F CFTR protein is unable to translocate to the plasma membrane where CFTR normally displays its physiological activity. Other mutations of human CFTR which may be cited are G542X, G551D, N1303K, W1282X, R553X, 621+1G, 1717-1G, R117H and R1162X. Over the 1900 different mutations that have been described, only four of these, besides Δ508F, represent more than 1% of cases.

In addition to the well-established role of CFTR in the function of pulmonary epithelial cells, the importance of CFTR in microbicide activity of pulmonary macrophages has been shown, as well as CFTR also augmenting the neutrophil microbicide capacity.

Therefore, one strategy aimed at developing novel molecules targeting the root cause of CF rather than disease symptoms, lies on the improvement of mutant CFTR functions.

Despite a tremendous effort in particular within said strategy made over the last two decades to understand pathogenesis of cystic fibrosis, there is no cure for the disease.

(R)-roscovitine is a potent cyclin-dependent kinase inhibitor that was initially proposed to be used for treating various cancers (see WO 97/20842).

(R)-roscovitine, (2-(R)-(1-ethyl-2-hydroxyethylamino)-6-benzylamino-9-isopropylpurine), which is a substituted derivative of purine, and closely related derivatives thereof, were shown to rescue some Δ508F CFTR plasma membrane translocation (see WO 2006/042949).

Nevertheless, it is still not clear why the cells of innate immune system including macrophages and neutrophils are unable to eradicate microbial infection. In the cystic fibrosis lung, microbial colonization, predominantly with *Pseudomonas aeruginosa*, and massive lung tissue damage by recruited neutrophils lead to severe bronchial damage, respiratory insufficiency, and death. Defects in innate immune system could have important consequences for microbial defence in cystic fibrosis patients.

Current treatment of cystic fibrosis relies upon treating microbial infections that are consequently appearing at one stage of this disease. Antimicrobials and more particularly antibiotics are largely used, with numerous drawbacks because of increasingly highly resistant microorganisms to the known antibiotics.

In order to develop an alternative strategy, the inventors investigated another pathway, in connection to alveolar macrophages (AMs), and identified compounds which could resolve microbial infection without the use of antimicrobials.

In order to perform their major function, macrophages must ingest and destroy microbial pathogens. Following engulfment of pathogens by phagocytosis, the phagosomes fuse with lysosomes into phago-lysosomes where pathogens are digested by various proteolytic and lipolytic enzymes. Optimal functioning of the lysosomal degrading enzymes requires an acidic pH, which characterizes the lysosomes lumen. Generation of low phago-lysosomes pH is primarily driven by the V-ATPases, proton pumps that use cytoplasmic ATP to load H+ into the organelle derived during lysosomes fusion to the maturing phagosomes.

It was recently shown that murine alveolar macrophages employ CFTR as a major charge shunt mechanism thereby allowing acidification of phago-lysosomal compartment and consequent bacterial killing (Deriy et al., 2009; Di et al., 2006).

Indeed it was shown that the intra-phago-lysosomal pH of alveolar macrophages of individuals having cystic fibrosis is less acidic (pH 7.2), as compared with those of healthy individuals (pH 5.2). It was further shown that there is a tight correlation between CFTR genotype and levels of lysosomal acidification and microbial killing.

Accordingly, there is a need for providing a method of treatment of cystic fibrosis condition in an individual in need thereof.

There is furthermore a need for providing a treatment for alleviating symptoms associated with cystic fibrosis condition in an individual in need thereof.

There is a need to provide a treatment of microbial infection that is most frequently associated with cystic fibrosis condition in an individual in need thereof.

There is a need to provide a treatment of microbial infection that is most frequently associated with cystic fibrosis condition, by limiting the use of antibiotics in an individual in need thereof.

There is also a need for providing a treatment for alleviating symptoms associated with cystic fibrosis condition in an individual in need thereof, said treatment being independent from the mutation of the CFTR encoding gene.

There is still a need to provide molecules rescuing the microbicide function in CF pulmonary alveolar macrophages (AMs).

M3 is a known metabolite of (R)-Roscovitine, which does not exhibit kinase inhibiting properties. It was in particular described in patent application WO 2004/016612.

SUMMARY OF THE INVENTION

Surprisingly, the inventors found that a subset of purine derivative compounds and substituted imidazo[4,5-b]pyridines derivatives has the capacity of restoring the microbicide properties of alveolar macrophages, this microbicide properties relying upon the acidification of the intra-phago-lysosomal pH of said alveolar macrophages.

In one of its aspect, the present invention therefore provides compounds of formula (I) as defined hereinafter for their use in the treatment of a disease characterized by a reduction in macrophage-mediated bacterial killing, particularly alveolar macrophages (AMs).

In a further object, the present invention more particularly focuses on said compounds of formula (I) for their use in the treatment of diseases involving pulmonary microbial infections and more particularly cystic fibrosis (CF).

LEGENDS OF THE FIGURES

FIG. 1. M3 metabolite and related derivatives potentiate phagosomal acidification in human alveolar macrophages.

(1A) DIC overlay of fluorescence image for alveolar macrophages following a 120-200 min loading with BioParticles®. Scale bars: 10 µm.

(1B1 and 1B2) Kinetics of acidification for representative compounds.

(1C) Comparative effect of various compounds on phagosomal pH in human alveolar macrophages. Data summary from 3-10 patients for each compound tested at 10 µM. Data was obtained in triplicate for each patient and averaged for all patients with error bars indicating the SEM. Data were normalized to fluorescence changes observed in untreated control cells for each patient before averaging.

Figure 2:
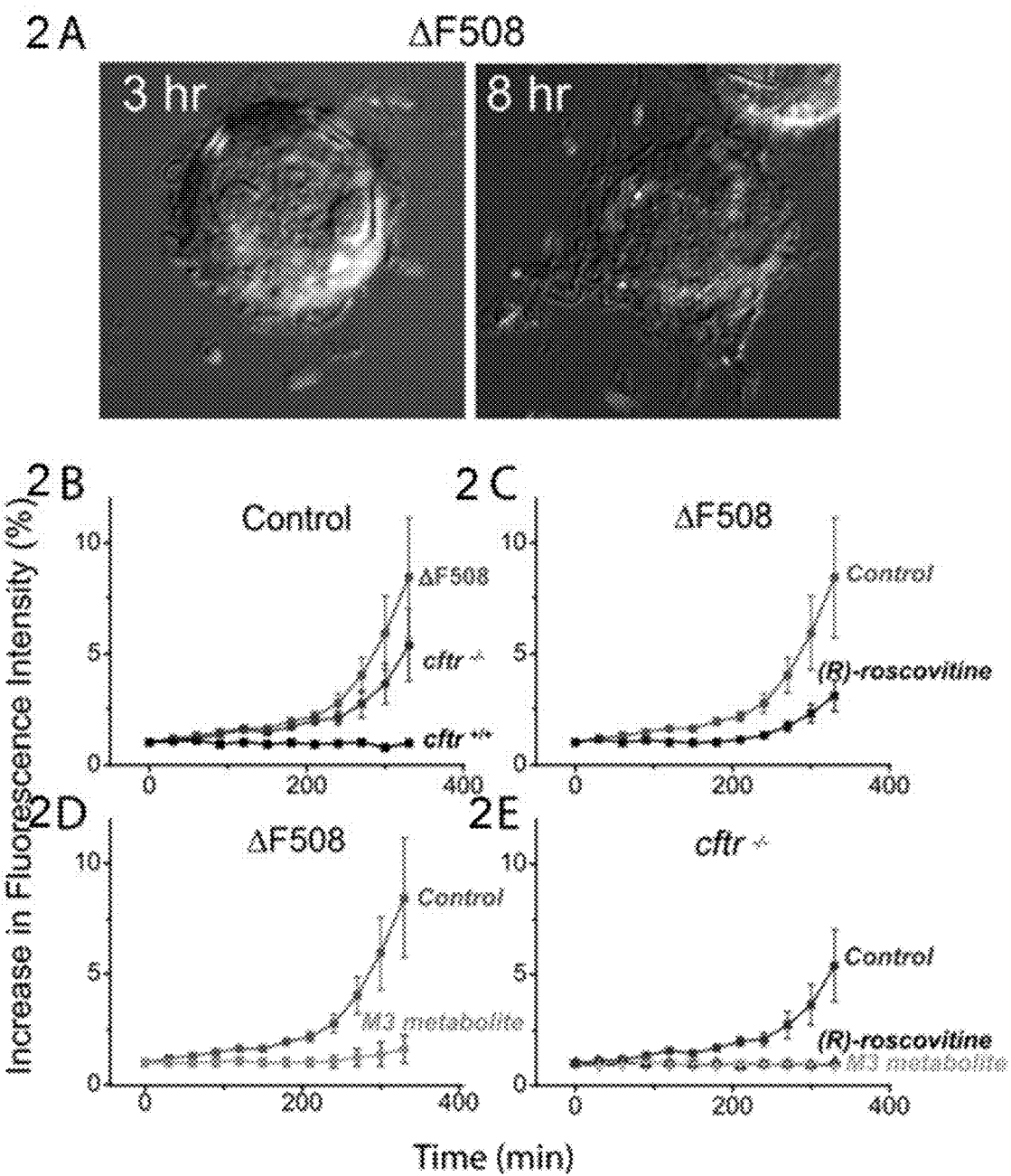

FIG. 2. Inhibition of *Pseudomonas aeruginosa* growth in cftr$^{-/-}$ and ΔF508 alveolar macrophages by M3 metabolite and derivatives. A comparison of intracellular bacterial growth in single murine alveolar macrophages was carried out using live cell microscopy. Cells were fed DS-Red expressing *P. aeruginosa* for 30 min (MOI<10). Cells were exposed to M3 metabolite for 20 min prior to exposure to bacteria. Adherent and non-ingested bacteria were then removed by washing and incubation with antibiotics and live alveolar macrophages were observed microscopically for approximately 6 hours.

(2A) Representative cells from ΔF508 CFTR mutant mouse with ingested bacteria at 3 and 8 hours after incubation. Intracellular localization of bacteria was confirmed by 3D reconstruction of confocal Z stacks of bacterial fluorescence and cellular reflection/backscatter.

(2B-2E) Summary data from at least 3 separate experiments comparing bacterial growth over time (assayed as mean DS-Red intensity at λ=607±20 (F)), per cell) between genotypes (2B); in ΔF508 CFTR alveolar macrophages in the presence and absence of 20 µM (R)-roscovitine (2C); in ΔF508 CFTR alveolar macrophages in the presence of 20 µM of M3 metabolite (2D); data from cftr$^{-/-}$ alveolar macrophages in the presence M3 metabolite are shown in (2E). The data are presented as means of fluorescence intensities±SEM. Control conditions summarized data obtained from: WT—2 mice, 38 cells; ΔF508—6 mice, 120 cells; cftr$^{-/-}$ 4 mice, 87 cells. In the presence of (R)-roscovitine data was obtained from: WT—1 mouse, 7 cells; ΔF508—5 mice, 91 cells; cftr$^{-/-}$ 1 mouse, 18 cells. In the presence of M3 metabolite we analysed data from: ΔF508—3 mice, 57 cells; cftr$^{-/-}$1 mouse, 67 cells.

Figure 3:
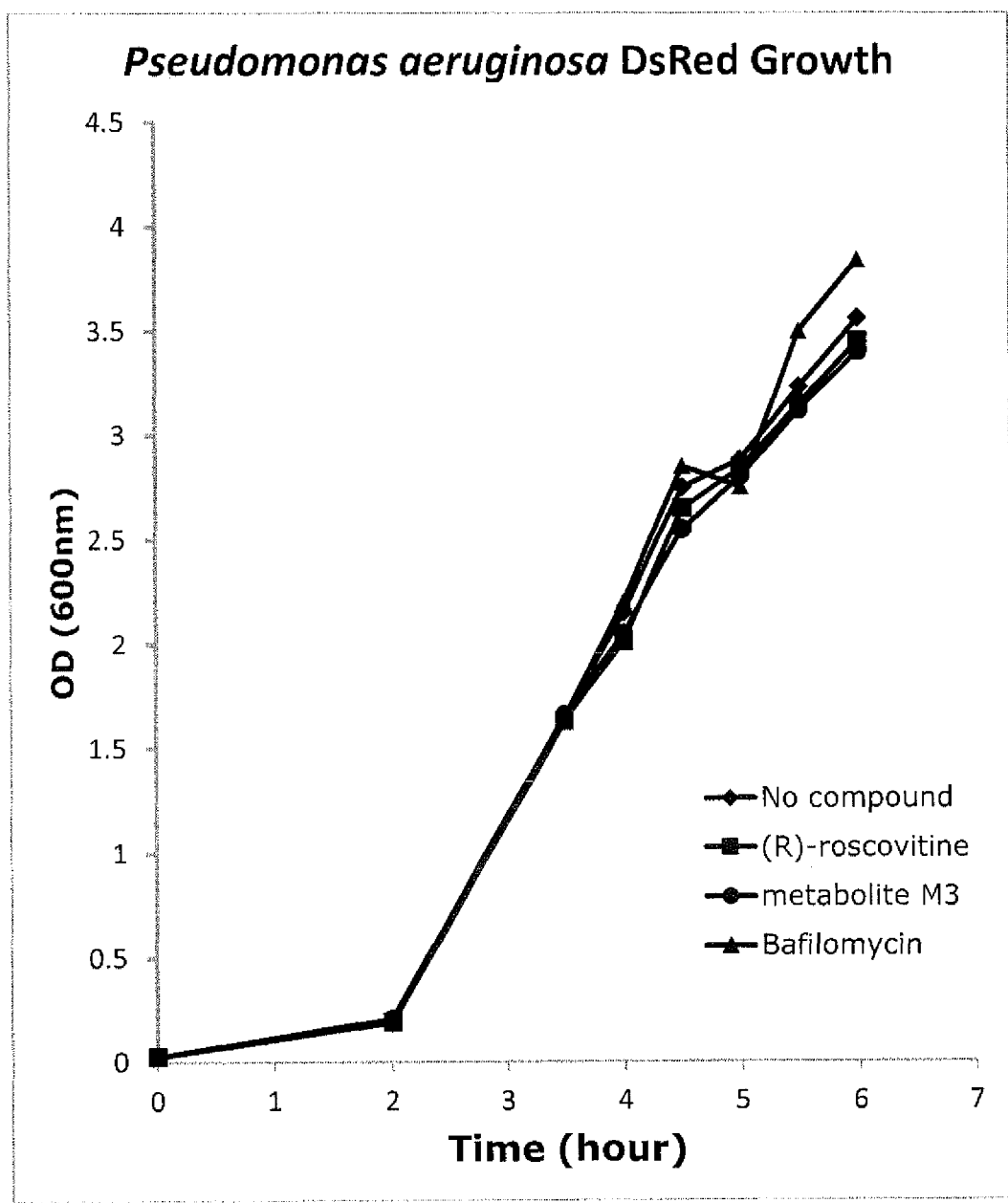

FIG. 3. Absence of growth inhibition of *P. aeruginosa* culture by M3 metabolite and derivatives. 1/100 dilution of an overnight culture of *P. aeruginosa* was introduced in fresh culture medium and cultures were incubated at 37° C. with 20 µM of M3 metabolite or derivatives or 1 µM bafilomycin (negative control). Optical density (600 nm) was measured 2 h and 3.5 h after starting the cultivation, and every 30 min for 2.5 h.

Figure 4:
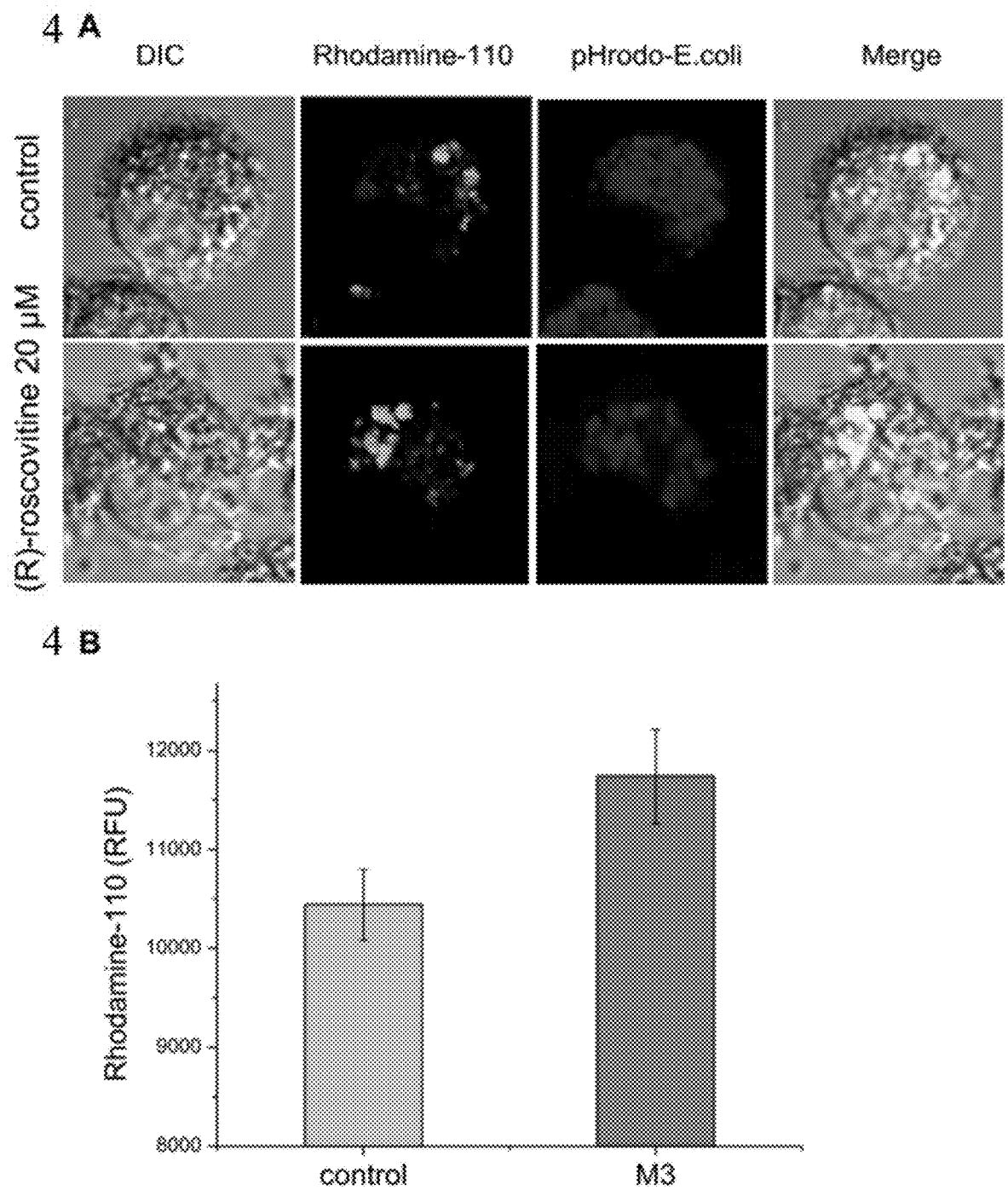

FIG. 4. M3 metabolite enhanced lysosomes fusion in murine alveolar macrophages.

(4A) Rhodamine-110, bis-(CBZ-L-Phenylalanyl-L-Arginine Amide), is cathepsin sensitive and selective non-fluorescent substrate that converts to fluorescent mono-amide upon the cleavage of the covalently linked peptide/amino acid. We added Rhodamine-110 to the cells prior the pHrodo-Red conjugated *E. coli* Bioparticles® providing simultaneous uptake of both probes into phagosomes. Lysosomes fusion into nascent phagosomes brings proteases including cathepsin and triggers Rhodamine conversion.

(4B) M3 metabolite (10 µM) enhanced lysosomes fusion in mouse alveolar macrophages over that observed in control cells following pHrodo-*E. coli* uptake.

DETAILED DESCRIPTION OF THE INVENTION

According to a first aspect, a subject matter of the present invention relates to a compound of formula (I):

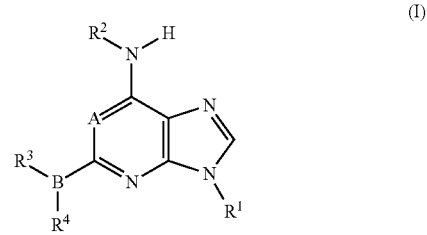

wherein

A is N or CH,

B is N O, or S, $R^1$ is

H, a $(C_1\text{-}C_4)$alkyl group, for example chosen among methyl, ethyl, propyl, 2propyl(isopropyl), preferentially being a 2-propyl(isopropyl), a methyl$(C_1\text{-}C_6)$cycloalkyl group for example chosen among methylcyclopropyl and methylcyclobutyl, or a $(C_1\text{-}C_6)$cycloalkyl group for example a cyclopropyl, $R^2$ is an aryl, said aryl group being optionally substituted by an halogen atom, an hydroxyl group, a methoxy group or an identical or different aryl group or a heteroaryl group, an arylmethyl group, in particular benzyl, and substituted benzyl with one to three groups, such as a $(C_1\text{-}C_3)$alkyl group, a OH, a OMe or an halogen group chosen among F, Cl and Br, or a methylheteroaryl group such as methylpyridine and methylthiophene, $R^3$ is absent when B is O or S, or is H or a $(C_1\text{-}C_4)$alkyl group when B is N, $R^4$ is a $(C_1\text{-}C_5)$alkyl group or a $(C_1\text{-}C_4)$cycloalkyl group, each group bearing a carboxylic acid group, and said $(C_1\text{-}C_5)$alkyl group or $(C_1\text{-}C_4)$cycloalkyl being optionally substituted by a hydroxyl group, a halogen group or a methoxy group, and when B is N, $R^3$ and $R^4$ can together form a 5- or 6-membered heterocycle substituted by a carboxylic acid group, and optionally substituted by a halogen atom, a hydroxyl group, a methoxy group or a hydroxymethyl group, or anyone of its pharmaceutically acceptable salt, for use in the treatment of a disease characterized by a reduction in macrophage-mediated bacterial killing.

When in formula (I) $R^2$ means an aryl group substituted by an identical or different aryl or heteroaryl group, it constructs a biaryl moiety.

In the framework of the instant invention, a "disease characterized by a reduction in macrophage-mediated bacterial killing" typically encompasses a disease for which macrophages, particularly alveolar macrophages, are impaired with respect with acidification of lyso-phagosomes hence resulting in a reduction of their abilities to kill bacteria.

In a particular embodiment, such a disease characterized by a reduction in macrophage-mediated bacterial killing is selected in a group comprising asthma, chronic obstructive pulmonary disease (COPD), cystic fibrosis, inflammatory asthma, pneumonia and tuberculosis.

In another particular embodiment, the compounds of formula (I) according to the present invention are used in the treatment of cystic fibrosis.

According to a particular embodiment, the treatment is intended for patients having cystic fibrosis and possessing anyone of the mutant forms of human CFTR.

According to a particular embodiment, the treatment is intended for patients having cystic fibrosis and possessing a mutation being the deletion of the ΔF508 in the gene encoding CFTR or possessing a mutation being a mutation different from the deletion of the ΔF508 in the gene encoding CFTR. The following other mutations may be cited as examples: G542X, G551D, N1303K, W1282X, R553X, 621+1G, 1717-1G, R117H and R1162X.

In a further particular embodiment, the compounds of formula (I) according to the present invention are used for the treatment of diseases involving pulmonary microbial infections or of pulmonary inflammatory diseases.

According to one aspect of the present invention, the compound of formula (I) according to the present invention may be useful to inhibit, prevent and/or treat lung infection by bacteria and other micro-organisms, which may or may not be a consequence of cystic fibrosis.

Among the bacteria in particular susceptible of infecting an individual having a cystic fibrosis one may consider a bacterium such as: a bacterium from the genus *Staphylococcus*, such as *S. aureus*; a bacterium from the genus *Haemophilus*, such as *H. influenzae*; a bacterium from the genus *Pseudomonas*, such as *P. aeruginosa*; a bacterium from the genus *Burkholderia*, for example *B. cepacia, B. multivorans, B. cenopacia, B. stabilis, B. vietnamensis, B. dolosa, B. ambifaria, B. pyrrocinia*; a bacterium from the genus *Mycobacterium*, such as *M. absessus, M. avium, M. tuberculosis*.

Anaerobic bacteria may be also considered within the scope of the instant invention, such as for example a bacterium from the genus *Prevotella, Veillonella, Propionibacterium, Actinomyces, Streptococcus*, for example *S. pneumonia, Legionnella*, for example *L. pneumophila*.

Other bacteria species may be considered within the scope of the instant invention, as for example: *Stenotrophomonas maltophilia, Achromobacter xylosoxidans, Ralstonia mannitolilytica, Ralstonia pickettii, Inquilinus limosus, Elizabethkingia meningoseptica*.

According to a particular embodiment, the disease characterized by a reduction in macrophage-mediated bacterial killing is a disease involving pulmonary microbial infection, which may be selected in a group comprising an infection by *Pseudomonas aeruginosa, Staphylococcus aureus, Burkholderia cepacia, Haemophilus* influenza and *Mycobacterium tuberculosis*.

Besides bacteria, another category of micro-organisms is susceptible of infecting an individual having a cystic fibrosis, namely fungi.

Among fungi, one may consider more particularly the filamentous fungi, for example *Aspergillus fumigatus*, which remains by far the most common agent of airway colonization, *Acrophialophora fusispora, Aspergillus terreus, Exophiala dermatitidis, Penicillium emersonii, Scedosporium apiospermum and Scedosporium prolificans*.

According to one aspect, the present invention relates to a compound of formula (I) as defined above, wherein the group $NHR^2$ may be chosen among one of the following groups:

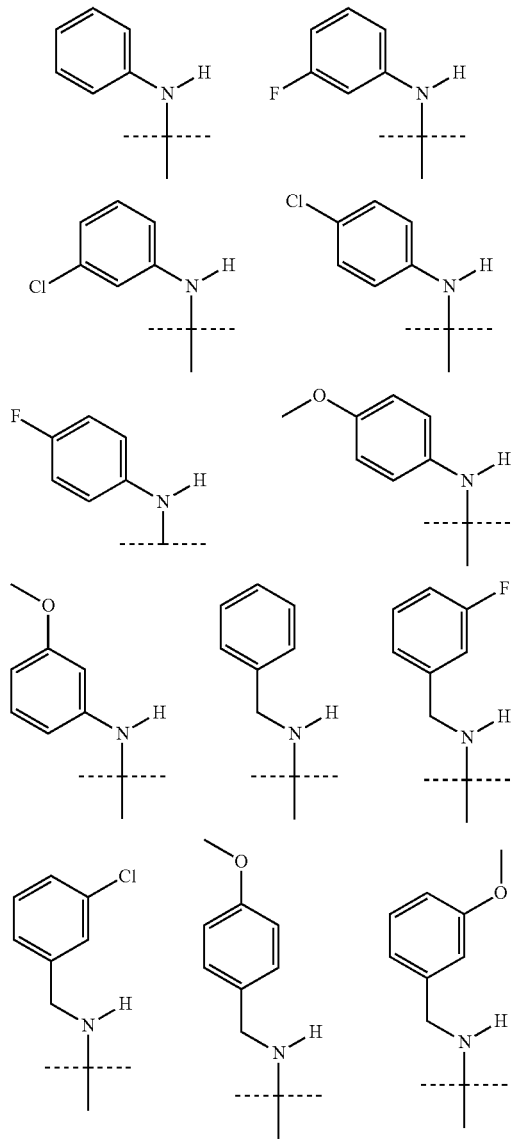

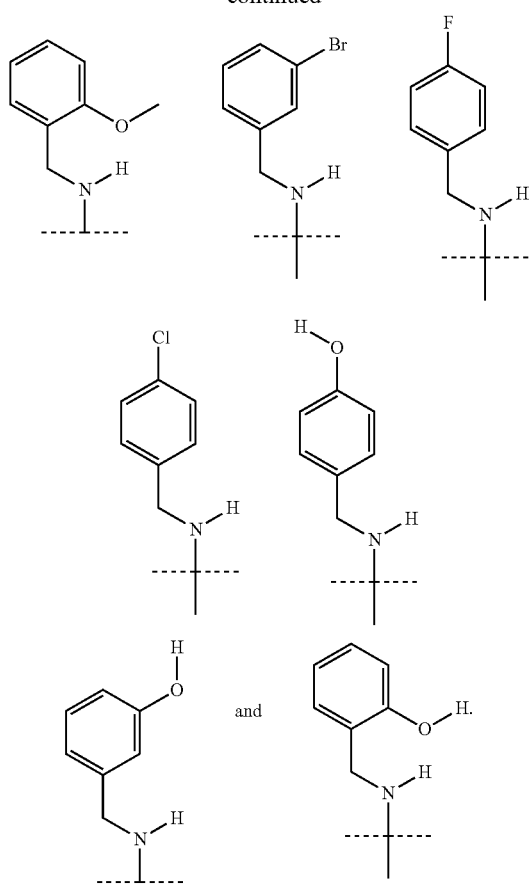
According to another aspect, the present invention relates to a compound of formula (I) as defined above, wherein B is N and the group NR³R⁴ is chosen among:
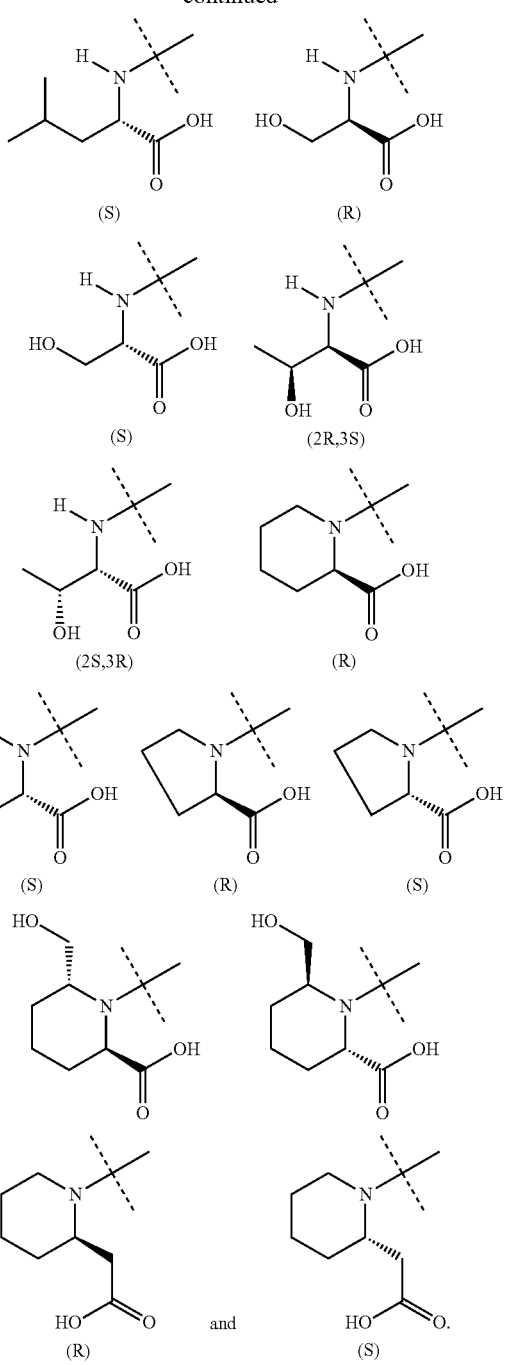
According to another aspect, the present invention relates to a compound of formula (I) as defined above, wherein B is O and OR⁴ is chosen among:
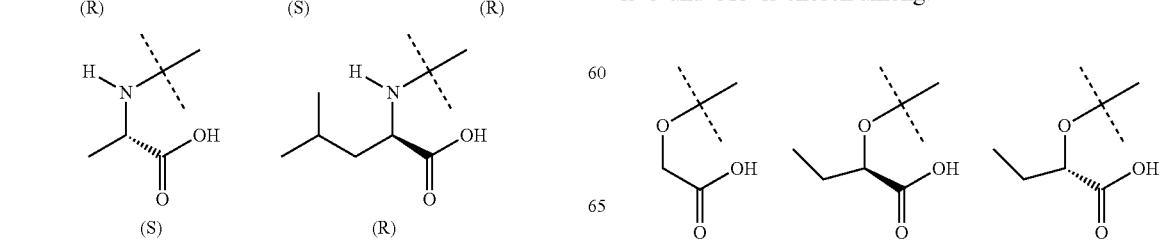

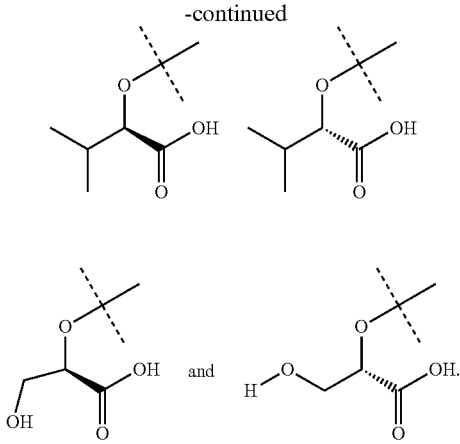

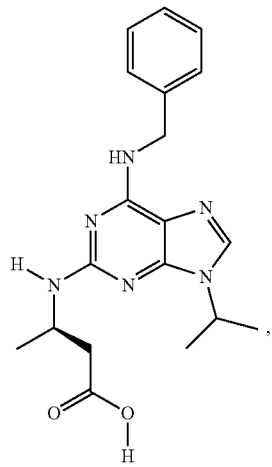

(4)

According to another aspect, the present invention relates to a compound of formula (I) as defined above, wherein $R^1$ represents a 2-propyl(isopropyl).

According to another aspect, the present invention relates to a compound of formula (I) as defined above, wherein $R^2$ represents a benzyl group.

According to another aspect, the present invention relates to a compound of formula (I) as defined above, wherein $R^3$ represents a hydrogen atom.

According to another aspect, the present invention relates to a compound of formula (I) as defined above, wherein $R^4$ represents a 1-carboxypropan-1-yl group.

According to another aspect, the present invention relates to a compound of formula (I) as defined above, wherein $R^1$ represents a 2-propyl(isopropyl), $R^2$ represents a benzyl group, $R^3$ represents a hydrogen atom and $R^4$ represents a 1-carboxypropan-1-yl group, in the (R) or (S) form or in the form of a racemic mixture thereof.

According to a more particular embodiment, the present invention particularly focuses on M3 or (2R)-2-[[9-isopropyl-6-(phenylmethylamino)purin-2-yl]amino]butanoic acid:

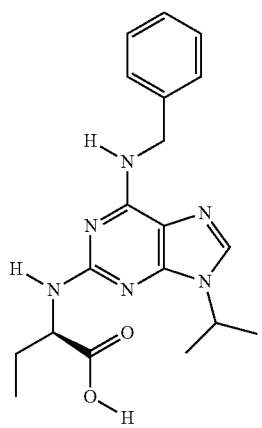 [SMILES: CC[C@@H](Nc1nc(NCc2ccccc2)c2ncn(C(C)C)c2n1)C(=O)O]

According to a further particular embodiment, the present invention particularly focuses on (3R)-3-[[6-(benzylamino)-9-isopropyl-purin-2-yl]amino]butanoic acid:

and on (2S)-2-[[6-(benzylamino)-9-isopropyl-purin-2-yl]amino]-3-hydroxy-propanoic acid:

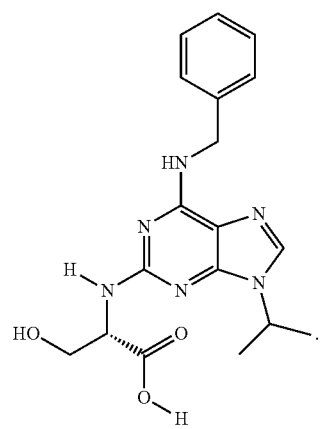

(6)

The present invention further extends to said two compounds (4) and (6) which are new and to any pharmaceutical composition containing them.

The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I) and/or salts thereof may form solvates (e.g. hydrates) and the invention includes all such solvates.

In the context of the present invention, the term:
"halogen" is understood to mean chlorine, fluorine, bromine, or iodine, and in particular denotes chlorine, fluorine or bromine,
"$(C_1-C_4)$alkyl", $(C_1-C_5)$alkyl and "$(C_1-C_6)$alkyl" as used herein respectively refers to $C_1-C_4$, $C_1-C_5$ or $C_1-C_6$ straight- or branched-saturated hydrocarbon chain Examples are, but are not limited to, methyl, ethyl, 1-propyl, 2-propyl, t-butyl,
"aryl" radicals are chosen from phenyl, naphthyl or indenyl, "heteroaryl" radicals comprise 3 to 10 ring members, optionally comprising one or more heteroatoms chosen from oxygen, sulfur and nitrogen, in particular, thiazolyl, thienyl, pyrrolyl, pyridinyl, furyl, imidazolyl, oxazolyl, pyrazinyl, tetrazolyl, oxadiazolyl, thiadiazolyl, isoxadiazolyl, isothiadiazolyl, isothiazolyl, isoxazolyl, triazolyl, pyrazolyl or indolyl, "heterocycle" radicals comprise 1 to 2 heteroatoms, and at least a nitrogen atom, and optionally another heteroatom chosen from oxygen, sulfur or nitrogen and represent in particular piperidinyl, morpholinyl, pyrrolidinyl, imidazolidinyl, pyrazolidinyl, isothiazolidinyl, thiazolidinyl, isoxazolidinyl, oxazolidinyl, piperazinyl, 2-piperidone, 3-piperidone, 4-piperidone, 2-pyrrolidone or 3-pyrrolidone;

"patient" may extend to mammal and non-mammal animals, preferably humans or non-human mammals, such as cats, dogs or cattle.

The compounds of formulae (I) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compounds of the present invention can be prepared by conventional methods of organic synthesis practiced by those skilled in the art. In particular, the starting material may be 6-chloro-2-fluoropurine. One possible process is illustrated in example 1 hereinafter.

When B is N, the introduction of amino acids on the 2 position of the purine scaffold can be performed according to the following scheme:

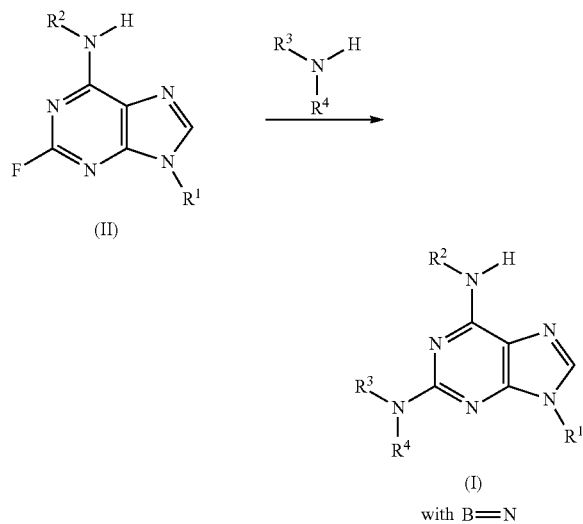

The substitution of the halogen in the compound of formula (II), wherein $R^1$ and $R^2$ are as defined above, may be performed by reacting it with a compound of formula $R^3R^4NH$, wherein $R^3$ and $R^4$ are as defined above, upon heating, for example 120 to 160° C., using a base in a limited amount, for example potassium triphosphate, in a solvent, for example DMSO. Said process step is simple and allows the introduction of a variety of amino acids. One other major advantage of said process step lies in the work-up that is simple as the compounds can be separated by crystallization or column chromatography on silica gel using mixture of solvent (eg: $CH_2Cl_2$-EtOAc-THF) as eluents and therefore the use of HPLC can be avoided.

According to a further embodiment, the present invention also relates to a pharmaceutical composition comprising a compound of formula (I) according to the present invention and a pharmaceutically acceptable carrier, for use in the treatment of a disease characterized by a reduction in macrophage-mediated bacterial killing.

In one preferred embodiment, the pharmaceutical composition is for use in the treatment of a disease selected in a group comprising asthma, chronic obstructive pulmonary disease (COPD), cystic fibrosis, inflammatory asthma, pneumonia and tuberculosis or a disease involving pulmonary microbial infection, which may be selected in a group comprising an infection by *Pseudomonas aeruginosa, Staphylococcus aureus, Burkholderia cepacia, Haemophilus influenza* and *Mycobacterium tuberculosis.*

The pharmaceutical composition according to the present invention may be suitable for oral, systemic, parenteral, intra-pulmonary, intra-bronchial or intra-alveolar administration.

A compound of formula (I) according to the invention may be formulated with excipients and components that are commonly used for oral compositions, as for example, fatty and/or aqueous components, humectants, thickeners, preserving agents, texture agents, taste agents and/or coating agents, antioxidants, preserving agents.

The formulating agents and excipients for an oral composition are known in this field and will not be the object of a fully detailed description herein. Many embodiments of oral compositions are formulated via usual processes for producing coated tablets, gel capsules, gels, controlled-release hydrogels, emulsions, tablets and capsules.

In another embodiment, a compound of formula (I) may be formulated in a pharmaceutical composition suitable for a systemic or a parenteral administration and in particular for an administration by injection. Parenteral administration comprises sub-cutaneous, intra-muscular and intra-venous administration. Formulations for injection may be presented in single-unit dosage form, such as ampoules or in multi-dose containers. The compositions may be formulated as suspensions, solutions or emulsions in oily or aqueous vehicles, and may contain additional agents, such as preservatives, emulsifying and/or stabilizing agents. Alternatively, a compound of formula (I) may be formulated as a dispersible powder, which may be prepared as a liquid composition, with a suitable vehicle, for example sterile water, just before use.

A compound of formula (I) may also be formulated as a rectal composition, such as for example a suppository, containing conventional suppository bases, such as cocoa butter or other glycerides.

In a most preferred embodiment, a compound of formula (I) may be formulated as an aerosol for intra-pulmonary, intra-bronchial or intra-alveolar administration.

As an example of devices suitable for implementing the present invention one may cite pressurized metered dose inhalers (pMDIs), dry powder inhalers (DPIs) and nebulizers, such as pressure-driven jet nebulizer or an ultrasonic nebulizer.

Any type of formulations adapted for such an aerosol administration is a common knowledge for a skilled in the art.

A compound of formula (I) may be formulated as a liquid solution a liquid suspension or a powder.

As for liquid solution or suspension, a carrier may be typically pyrogen-free sterile or a dilute aqueous alcoholic solution. Liquid solution or suspension are preferably isotonic, hence may comprise sodium chloride. Optional additives include one or more preservative(s), such as for example methyl hydroxybenzoate, one or more antioxidant(s), one or more flavouring agent(s), one or more volatile oil(s), one or more buffering agent(s) and one or more surfactant(s).

As for a powder formulation, commonly used ingredients, such as a powdered diluent, for example powdered lactose, and surfactant(s) may be added.

Metered dose inhalers are pressurized aerosol dispensers, typically comprising a solution or a suspension of the active ingredient, namely a compound of formula (I), and a liquefied propellant. Suitable propellants include propellants commonly used in the art, such as for example chlorofluorocarbon compounds, in particular, dichlorodifluoromethane, trichlorofluoromethane, dichlorotetrafluoroethane and mixtures thereof.

Suitable formulations may also comprise one or more co-solvent(s), such as for example, ethanol, one or more surfactant(s), such as oleic acid and sorbitan trioleate, one or more antioxidant(s) and one or more suitable flavouring agent(s).

A dosage regimen suitable for the administration of a compound of formula (I) falls within the technical skills of an artisan in the art, and depends from multiple parameters. Indeed, a suitable dosage regimen depends from the gender, the age, the weight, and the progress of the disease. Within the scope of the instant invention, a suitable dosage regimen may encompass about 1 to 500 mg of the active compound.

For example, for an oral administration, a drug may comprise about 1 to about 500 mg of active compound, for example about 20 to about 250 mg of active compound, for example about 50 to 150 mg of active compound.

For example, for an aerosol mode of administration, the active compound may be administrated from about 1 to about 100 mg per inhalation.

In another embodiment, the pharmaceutical composition according to the present invention may be administered prior, during or after another pharmaceutical composition comprising an additional agent.

In a further embodiment, the pharmaceutical composition according to the present invention may comprise an additional agent.

Said additional agent may in particular be an antibiotic suitable to relieve or alleviate microbial infection.

Such antibiotic may be selected in a group comprising amikacin, amoxicillin, azithromycin, aztreonam, cefalotin, ceftazidim, ciprofloxacin, clarithromycin, colimycin, colistin, fosfomycin, gentamicin, imipenem, levofloxacin, meropenem, netilmicin, piperacillin, rifampicin, sulbactam, tazobactam, ticarcillin, tobramycin, a derivative thereof and a mix thereof.

In another embodiment, the additional agent may be a mucolytic agent, a bronchodilator, a bacteriophage, an anti-inflammatory agent or an anti-infective agent.

A mucolytic agent may be selected among acetylcysteine, ambroxol, bromhexine, carbocisteine, domiodol, dornase alfa, eprazinone, erdosteine, letosteine, mannitol, neltenexine, sobrerol, stepronin, tiopronin.

A bronchodialator may be selected among albuterol, metaprotenerol sulfate, pirbuterol sulfate, salmeterol and tetrabuline sulfate.

A bacteriophage is suitable to relieve or alleviate microbial infection.

Suitable bacteriophage may be a myovirus, for example φNH-4 and a podovirus, for example φMR299-2, as described by Alemayehu et al. (2012).

Other bacteriophage may also be found as suitable within the scope of this invention, for example in Cooper et al. (2013); Soothill (2013); Henry et al. (2013).

An anti-inflammatory agent may be suitable to relieve or alleviate tissue inflammation that may appear during the microbial infection. Such anti-inflammatory agent may be selected in a group comprising a steroid compound and a non-steroid compound.

Among steroid compounds, one may use cortisol, betamethasone, dexamethasone, prednisone or prednisolone.

Among non-steroid compounds, one may use ibuprofen, sildenafil.

In one aspect, the invention provides a method for the treatment of a disease characterized by a reduction in macrophages-mediated bacterial killing, comprising the administration to a patient in need thereof of a compound of formula (I) according to the present invention, and in particular of compound M3.

In one embodiment, the disease characterized by a reduction in macrophage-mediated bacterial killing is selected in a group comprising asthma, chronic obstructive pulmonary disease (COPD), cystic fibrosis, inflammatory asthma, pneumonia and tuberculosis.

Yet, in a most particular embodiment, the disease characterized by a reduction in macrophage-mediated bacterial killing is cystic fibrosis.

In another embodiment, the individual is selected in a group comprising a mammal and a non-mammal animal, preferably a mammal animal, more preferably a human.

In certain embodiments, the patient possesses mutant forms of human CFTR.

In a particular embodiment, the patient possesses a mutant form of human CFTR being the Δ508F mutation or being different from the Δ508F mutation.

Within the scope of the instant invention, the compounds of formula (I) that are described herein are susceptible to be used for diagnosing diseases other than cystic fibrosis, provided these diseases have impaired acidification of lysophagosomes in macrophages.

Hence, in another aspect, the instant invention relates to a method for diagnosing disease characterized by a reduction in macrophage-mediated bacterial killing in an individual, said method comprising the steps of:
a) providing isolated macrophages from said individual;
b) incubating said macrophages with a microorganism able to provoke a pulmonary disease;
c) assessing the abilities of said macrophages to kill said microorganism.

Said method may also be called a method of determining phagosome bacterial killing function or phagosome acidification.

In a preferred embodiment, macrophages may be alveolar macrophages.

In a still preferred embodiment, alveolar macrophages may be collected by broncho-alveolar lavage or a biopsy of the lung epithelium.

In an another embodiment, the invention relates to a method for identifying a patient with an increased likelihood of responding to a compound of formula (I), wherein the patient has been diagnosed with or is at risk of developing a pulmonary infection, said method comprising:
a) providing isolated macrophages from said individual;
b) incubating said macrophages with a microorganism able to provoke a pulmonary disease;

c) providing to said macrophages an effective amount of a compound of formula (I);

d) assessing the abilities of said macrophages to kill said microorganism.

Methods for Measuring Intra-Phago-Lysosomal pH

Some specific dye compounds may serve as specific sensors of phagocytosis and further indicate whether the phago-lysosomal compartment is functional, i.e. has a proper pH value of about 5.2. For example, the dye compound may be almost non-fluorescent at neutral pH and may fluoresce in an acidic environment, hence displaying a low pKa.

Example of useful dye compounds to be used in the instant invention may be those commercially available under the name pHrodo® Red, pHrodo® Green from Life technologies; LysoSensor® Yellow/Blue, LysoSensor® Blue, LysoSensor® Green, Oregon Green from Molecular Probes.

These dye compounds may further be conjugated to bacteria, for example pHrodo Red *E. coli* BioParticles®, or large molecule, such as zymosan and dextran 10,000.

The related fluorescence may be assessed by flow cytometry, microscopy, spectroscopy or any suitable method known from a skilled artisan.

EXAMPLES

Example 1: Synthesis of 3-[[6-(benzylamino)-9-isopropyl-purin-2-yl]amino]butanoic acid

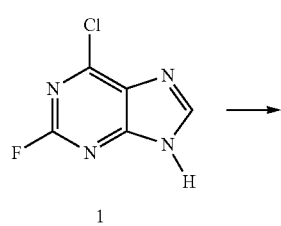

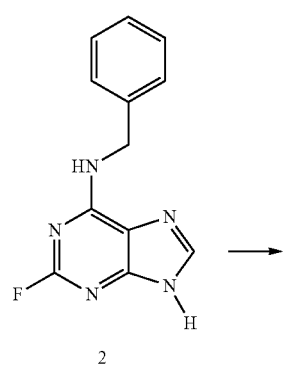

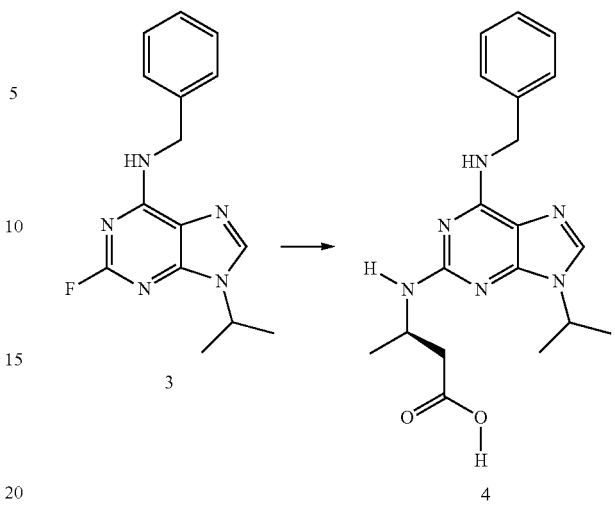

6-Benzylamino-2-fluoropurine (2) and N-benzyl-2-fluoro-9-isopropyl-purin-6-amine (3) were prepared starting from 6-chloro-2-fluoropurine using a procedure starting from 2,6-dichloropurine (Oumata et al. 2009).

6-Benzylamino-2-fluoropurine (2)

Mp 250° C. 1H-NMR (DMSO$_{-d6}$, δ ppm) 4.63 (brd, 2H, CH$_2$); 7.31 (m, 6H, C$_6$H$_5$ and 8-H).

N-benzyl-2-fluoro-9-isopropyl-purin-6-amine (3)

Mp 153° C. 1H-NMR (CDCl$_3$, δ ppm) 1.59 (d, 6H, J=6.5 Hz, CH(CH$_3$)$_2$); 4.75 (hept, 1H, CH(CH$_3$)$_2$); 4.83 (brs, 2H, CH$_2$); 6.61 (Brs, 1H, NH); 7.31 (m, 5H, C$_6$H$_5$), 7.67 (s, 1H, H-8).

(3R)-3-[[6-(Benzylamino)-9-isopropyl-purin-2-yl]amino]butanoic acid (4)

A mixture of N-benzyl-2-fluoro-9-isopropyl-purin-6-amine (0.5 g, 1.7 mmol) and 3-aminobutanoic acid (1.26 g, 12.26 mmol), K$_3$PO$_4$ (0.743 g, 3.50 mmol) in 1 ml DMSO was heated at 160° C. during 5 h. After cooling to 20° C. the mixture was diluted with 5 mL citric acid (10% in water, m:v). The mixture was extracted with EtOAC and the combined organic layers were washed with satured NaCl and dried over Na$_2$SO$_4$. After evaporation of the solvent in vacuo, the crude product was purified by crystallization from Ethyl acetate to afford 0.45 g of 4. Compound 4 could also be purified on silica gel using CH$_2$Cl$_2$-EtOAc-THF (6:2:1); $^1$H-NMR (DMSO-d$_6$, 400 MHz): 1.13 (d, 3H, J=Hz, CH$_3$CH); 1.46 (d, 6H, J=Hz, iPr); 2.40 (m, 2H, CH$_2$COOH); 4.26 (p, 1H, CHCH$_3$); 4.51 (hept, 1H, CH(CH$_3$); 4.62 (brs, 2H, CH$_2$C$_6$H$_5$); 6.14 (d, 1H, NH); 7.21, 7.27, 7.29 (t, t and d, 5H, C$_6$H$_5$), 7.79 (s, 1H, 8-H).

Example 2: Synthesis of (2R)-2-[[6-(benzylamino)-9-isopropyl-purin-2-yl]amino]butanoic acid. 5=Compound M3

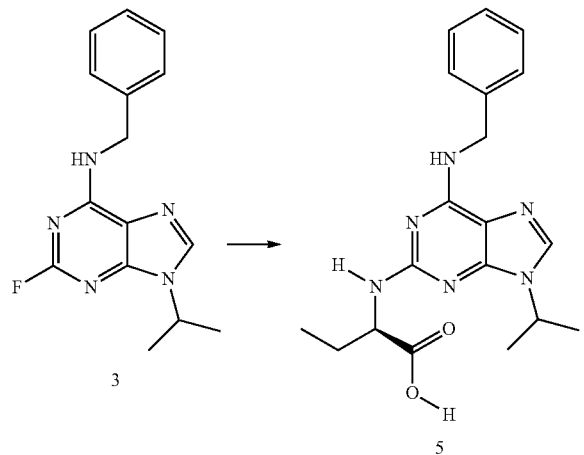 [SMILES: CC(C)n1cnc2c(NCc3ccccc3)nc(F)nc21 ; CC[C@@H](Nc1nc(NCc2ccccc2)c2ncn(C(C)C)c2n1)C(=O)O]

In the same conditions the fluoropurine 3 could be reacted with (R)-2-aminobutanoic acid to afford product 5.

$^1$H-NMR (DMSO-d$_6$, 400 MHz): 0.99 (t, 3H, J=6.5 Hz, CH$_3$—CH$_2$); 1.51 (d, 6H, J=6.5 Hz, CH(CH$_3$)$_2$); 1.78 (m, 2H, CH$_2$CH$_3$); 4.24 (m, 1H, CHN); 4.59 (hept, 1H, CH(CH$_3$); 4.71 (brs, 2H, CH$_2$C$_6$H$_5$); 6.43 (brs, 1H, NH); 7.32, 7.34 and 7.36 (t, t and d, 5H, C$_6$H$_5$); 7.86 (s, 1H, 8-H), 12.4 (brs, 1H, COOH).

Example 3: Synthesis of (2S)-2-[[6-(benzylamino)-9-isopropyl-purin-2-yl]amino]-3-hydroxy-propanoic acid (6)

In the same conditions, compound 6 by reacting 3 with L-serine to afford compound 6.

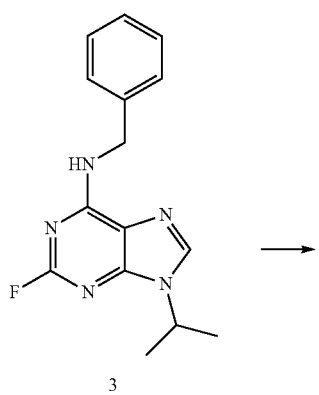

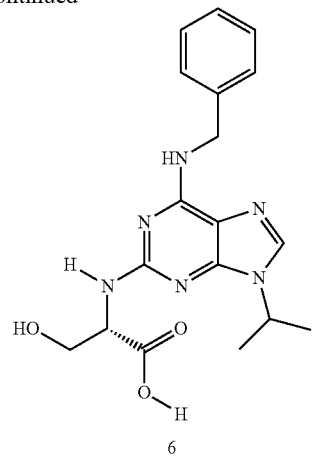

Mp 120-130° C. $^1$H-NMR (DMSO-$_{d6}$, δ ppm): 1.47 (d, 1H, J=6.5 Hz, CH(CH$_3$)$_2$); 3.83 (m, 2H, CH$_2$OH); 4.38 (m, 1H, CH—N); 4.51 (hept, 1H, CH(CH$_3$)$_2$); 4.62 (brs, 2H, CH$_2$C$_6$H$_5$) 7.21, 7.28, 7.36 (t, t and d, 5H, C$_6$H$_5$), 7.82 (s, 1H, 8-H); 12.35 (brs, 1H, COOH). $^{13}$C-NMR (DMSO-$_{d6}$, δ ppm): 174.1 (COOH).

Example 4: M3 Metabolite and Related Derivatives Potentiate Phagosomal Acidification in Human Alveolar Macrophages

1) Material and Methods

Broncho-alveolar lavage from humans was performed on consenting adults following a protocol approved by The University of Chicago Institutional Review Board. The patients included men and women, smokers and non-smokers, undergoing bronchoscopy for cancer biopsies prior to clinical treatment. The procedures used for the collection, isolation, and culture of human alveolar macrophages have been previously described (Nelson et al., 1985).

In brief, broncho-alveolar lavage fluid was strained through a 70 μm sterile cell strainer into a 50 ml conical tube centrifuge tube with a maximum broncho-alveolar lavage volume of 40 ml and a minimum volume of 10 ml followed by centrifugation at 1000×g for 5 min at 4° C. The broncho-alveolar lavage supernatant was then discarded and the cell pellet resuspended in 0.1-0.3 ml of cold complete media: DMEM, 10% FBS, 1% penicillin-streptomycin. Cells were counted on Countess® (Invitrogen) with a distribution cut-off of 20-60 μm and cell viability determined by trypan blue exclusion.

In general, the total number of macrophages per broncho-alveolar lavage was between 10$^4$ and 2×10$^5$. Cells were either plated on MatTek® glass bottom dishes for live cell video-microscopy as above or in 96- or 384-multi-well plates depending upon yield and experimental need. Multi-well plates were seeded at a density of 5-10×10$^3$ cells per well depending upon yield. Patient cells were not pooled and were maintained in individual cultures. Cells were incubated undisturbed for at least 3 hours to allow for macrophage attachment. After 3 h, medium was aspirated from each well or dish and cells were washed gently twice with fresh, warmed complete media to remove all non-adherent cells. Adherent cells were ≥98% viable and CD68 positive.

After 24 h incubation cells were exposed to pHrodo Red BioParticles® (Life Technologies). Acidification was measured on 96-well plate format with 560 and 580 nm excitation and emission wavelengths at 37° C. in a Synergy MX, BioTek® plate reader. In order to synchronize phagocytosis the plate was centrifuged (300×g) for 3 min after pHrodo Red BioParticle® addition.

2) Results

Figure 1B:
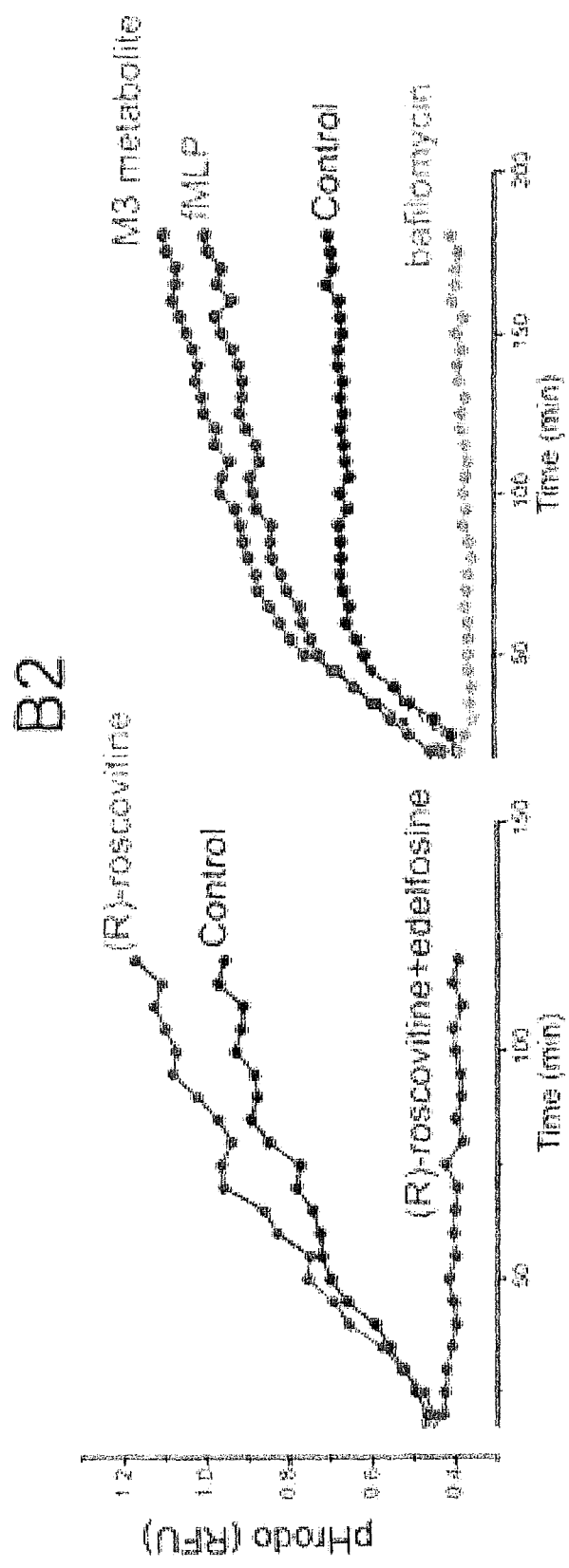
Figure 1C:
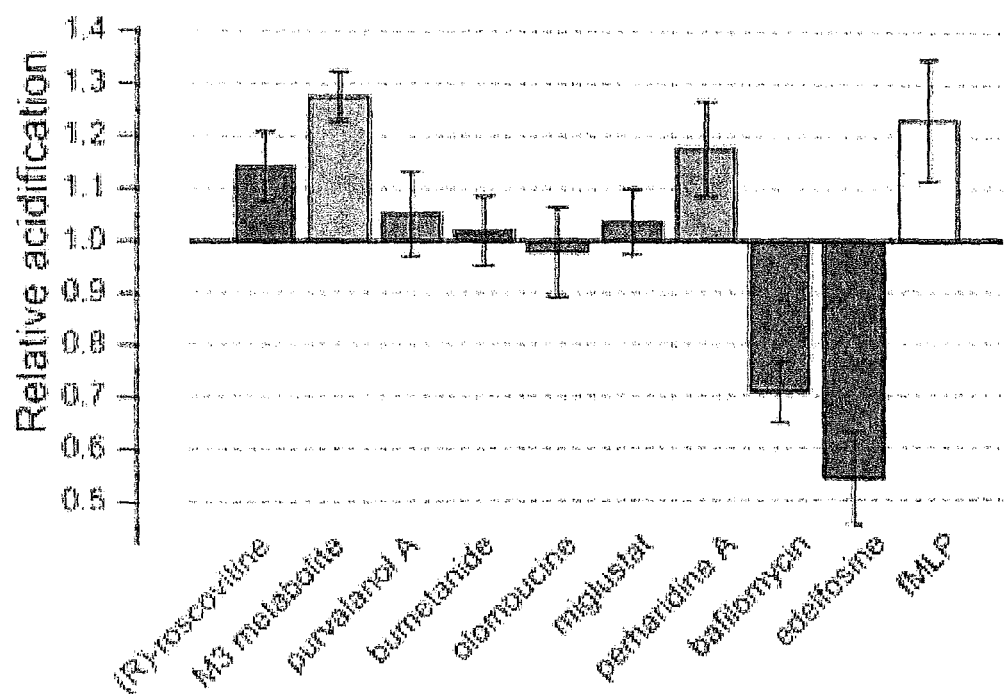

Phagosomal acidification is a prerequisite for efficient bacterial killing (Hackam et al., 1997), thus, several compounds were assessed for enhanced phagosomal acidification upon internalization of bioparticles conjugated to the pH sensitive dye pHrodo Red BioParticle® as depicted in FIGS. 1A-1C. Human alveolar macrophages were isolated from bronchoalveolar lavage, plated in multi-well plates and fed with pHrodo Red BioParticle® conjugated lyophilized *E. coli* (FIG. 1A). The kinetics of phagosomal acidification were read in a plate reader over a period of 3 h.

(R)-roscovitine, M3 metabolite and related purines are identified as compounds that significantly enhance acidification (FIGS. 1-B1-1C) over phagosomal pH observed in untreated cells. Negative controls in the screen included the V-ATPase inhibitor bafilomycin (Baf), and the potent phospholipase C inhibitor edelfosine (ET-18-OCH$_3$). Edelfosine has been previously also shown to prevent phagocytic uptake at the level of actin assembly.

Although (R)-roscovitine is a potent cyclin-dependent kinase inhibitor, surprisingly M3 metabolite does not share this feature (see Table 1 below).

TABLE 1

IC$_{50}$ value of (R)-roscovitine and M3 metabolite towards inhibition of various kinases.

| Kinases | (R)-roscovitine | Metabolite M3 |
| --- | --- | --- |
| CDK1/cyclin B | 0.42 | 11 |
| CDK2/cyclin A | 0.14 | 23 |
| CDK5/p25 | 0.22 | 41 |
| CDK9/cyclin T | 0.59 | >10 |
| CK1δ/ε | 1.7 | 21 |
| LmCK1 | 5.1 | >100 |
| CK2 | >100 | >100 |
| CLK1 | 1.3 | 18 |
| CLK2 | 0.69 | 14 |
| CLK3 | 17 | 52 |
| CLK4 | 0.69 | 19 |
| DYRK1A | 2.2 | 19 |
| DYRK1B | 2.1 | 22 |
| DYRK2 | 2.3 | 23 |
| DYRK3 | 59 | >100 |
| GSK-3α/β | 51 | >100 |
| PfGSK-3 | 11 | >100 |
| Pim1 | >100 | >100 |

These results suggest that the pathway of kinase inhibition is not involved in the mechanism leading to acidification of macrophage lyso-phagosomes.

Example 5: Inhibition of Bacterial Growth in cftr$^{-/-}$ and ΔF508 Alveolar Macrophages by Metabolite M3

1) Material and Methods

CFTR null mice, or cftr$^{-/-}$ (STOCK Cftr <tm1Unc>/TgN (FABPCFTR) # Jaw/Cwr and ΔF508 mutant mice (C57BL/6 Cftr <tm1Kth>/TgN(FABPCFTR) #J aw/Cwr homozygous for ΔF508 (van Heeckeren et al., 2004) breeding pairs were originally purchased from Case Western Reserve University's Cystic Fibrosis Animal Core. These mice express the hCFTR protein in the gut under the influence of the rat FABP promoter and are referred to as "gut corrected". CFTR null mice (cftr$^{-/-}$) were bred as homozygotes, ΔF508 mutant mice were bred as heterozygotes. All animals were housed in a specific pathogen-free biohazard level 2 facility maintained by The University of Chicago Animal Resources Center (Chicago, Ill.). Animal genotyping was performed by Transnetyx, Inc., (Cordova, Tenn.).

2) Results

We have shown previously that alveolar macrophages from cftr$^{-/-}$ and ΔF508 CFTR mice are defective in bacterial killing (Deriy et al., 2009; Di et al., 2006). Given the tight coupling between phago-lysosomal acidification and bacterial killing, we examined whether M3 metabolite and derivatives thereof could restore bacterial killing in alveolar macrophages from cftr$^{-/-}$ and ΔF508 CFTR expressing mice.

Cultured alveolar macrophages were exposed to (R)-roscovitine, M3 metabolite and derivatives thereof (20 μM) for 30 min prior to exposing cells to DS-red expressing *Pseudomonas aeruginosa*. Cells were allowed to ingest bacteria in the continued presence of the purine derivative compound to be tested and were observed in live cell video microscopy over a 6 h period for an increase in fluorescence indicative of bacterial growth either in the phagosome or in the cytoplasm following release from the phagosome (FIG. 2A).

Intracellular bacterial growth, measured as an increase in fluorescent intensity as a function of genotype is seen in FIG. 2B. As expected, ΔF508 CFTR expressing cells and cftr$^{-/-}$ cells showed bacterial growth, hence are confirmed being defective in bacterial killing.

In contrast, wildtype cftr$^{+/+}$ cells present no fluorescence increase, suggesting an absence of bacterial growth. Data in FIG. 2C demonstrate that (R)-roscovitine significantly rescues bacterial killing in ΔF508 CFTR expressing cells as well as in cftr$^{-/-}$ cells (FIG. 2E) to levels similar to that seen in cftr$^{+/+}$.

Surprisingly, data in FIGS. 2D and 2E using a kinase-inactive M3 metabolite showed that rescue of bacterial killing is at least as efficient as with (R)-roscovitine.

Example 6: M3 Metabolite Rescues Phagolysosomal Microbicidal Activity and does not Act as an Antimicrobial Compound In order to assess whether the killing effect of M3 metabolite towards bacterial cells are an indirect or a direct effect, bactericidal activity M3 metabolite and derivatives thereof was tested on bacterial cells.

1) Methods

*Pseudomonas aeruginosa* DsRed from single colony was grown in gentamicin containing TSB overnight at 37° C. with agitation at 300 RPM. Next day it was started the new culture at 1/100 dilution and certain compound of blocker were added to the tubes. We measured optical density (660 nm) of bacterial culture at every 30 minutes.

2) Results

Both M3 metabolite and its derivatives were unable to prevent bacterial growth when added at following concentrations: 20 μM (R)-roscovitine, metabolite M3, or 1 μM bafilomycin (FIG. 3).

Example 7: 4) M3 Metabolite Enhanced Lysosomes Fusion in Murine Alveolar Macrophages 1) Methods Isolated mouse alveolar macrophages (from cftr$^{-/-}$ or Δ508F CFTR mice) were cultured adherent on the poly-L-lysine coated glass bottom dishes for 24-48 h. Then they were treated with 10 μM Rhodamine-110 for 20 min at room temperature in the dark with following incubation with 0.1 mg/ml pHrodo-Red conjugated *E. coli* Bioparticles® for 1 hour at 37° C. Rhodamine-110, bis-(CBZ-L-Phenylalanyl-L-Arginine Amide), is cathepsin sensitive and selective non-fluorescent substrate that converts to fluorescent monoamide upon the cleavage of the covalently linked peptide/amino acid. Then the cells were washed twice with PBS, fixed with 4% PFA. The images were acquired immediately after fixation on Leica SP5 2-photon laser confocal microscope with a 63× (NA1.4) oil objective.

Isolated mouse macrophages were plated on 96-well plate with a density of 3-6,000 cells (20-60 μm diameter) per well, incubated in complete DMEM (10% FBS, 1% penicillin-streptomycin) at 37° C. under 5% $CO_2$ pressure for 24-48 h. The cells were loaded with 5 μM Rhodamine-110 for 20 min at room temperature in the dark, fed with *E. coli* Bioparticles® conjugated to pHrodo-Red for 1 h at 37° C. Rhodamine-110 signal was read in Synergy MX, Biotek plate reader with excitation 498 nm and emission 521 nm wavelengths.

2) Results

FIG. 4A shows that in the presence of R-roscovitine, the fluorescence resulting from rhodamine-110 processing by lysosomal proteases is increased as compared to the control assay performed in the absence of R-roscovitine. At the same time, fluorescence from pHrodo-Red conjugated *E. coli* Bioparticles® phagocytosis in alveolar macrophages are decreased in the presence of R-roscovitine, suggesting that phagocytosis of bacterial cells was followed by bacterial killing.

FIG. 4B shows that M3 metabolite allows rhodamine-110 processing by lysosomal proteases in an increased manner as compared to condition in which M3 metabolite is absent.

These results indicate that (R)-roscovitine and M3 metabolite allows for increased lysosomal activity.

REFERENCES

Patent References

WO 97/20842
WO 2004/016612
WO 2006/042949

Non Patent References

Alemayehu et al. Bacteriophages φMR299-2 and φNH-4 Can Eliminate *Pseudomonas aeruginosa* in the Murine Lung and on Cystic Fibrosis Lung Airway Cells. mBio 3:2 March/April 2012; doi:10.1128.
Cooper et al. Stability and purity of a bacteriophage cocktail preparation for nebulizer delivery. Lett Appl Microbiol. 2013 Sep. 25. doi: 10.1111/lam.12161.
Deriy et al. Disease-causing Mutations in the Cystic Fibrosis Transmembrane Conductance Regulator Determine the Functional Responses of Alveolar Macrophages, Journal of Biological Chemistry, 284, 51, 35926-35938, 2009.
Di et al. CFTR regulates phagosomes acidification in macrophages and alters bactericidal activity. Nat. Cell Biol. 2006; 8, 933-9442006.
Hackam et al. Regulation of phagosomal acidification. Differential targeting of Na+/H+ exchangers, Na+/K+-ATPases, and vacuolar-type H+-Atpases. The Journal of biological chemistry 1997; 272, 29810-29820.
Henry et al. Predicting in vivo efficacy to guide the choice of therapeutic bacteriophages to treat pulmonary infections. Antimicrob Agents Chemother. 2013 Sep. 16.

Nelson et al. Immunoglobulin G-induced single ionic channels in human alveolar macrophage membranes. Journal of Clinical Investigation 1985; 76, 500-507.
Oumata et al. Practical synthesis of roscovitine and CR8. Organic Process Res. And Dev. 2009, 13:641-644.
Soothill. Use of bacteriophages in the treatment of *Pseudomonas aeruginosa* infections. Expert Rev Anti Infect Ther. 2013 September; 11(9):909-15.
Van Heeckeren et al. Role of Cftr genotype in the response to chronic *Pseudomonas aeruginosa* lung infection in mice. Am J Physiol Lung Cell Mol Physiol 2004; 287, L944-952.

The invention claimed is:

1. A method for the treatment of a disease characterized by a reduction in macrophages-mediated bacterial killing, comprising the administration to a patient in need thereof of a compound of formula (I):

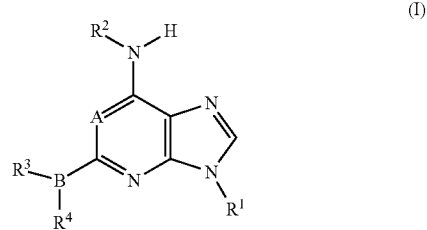

or pharmaceutically acceptable salts thereof,
wherein
A is N or CH,
B is N, O, or S,
$R^1$ is
  H,
  a $(C_1-C_4)$alkyl group,
  a methyl$(C_3-C_6)$cycloalkyl group, or
  a $(C_3-C_6)$cycloalkyl group,
$R^2$ is
  an aryl, said aryl group being optionally substituted by an halogen atom, an hydroxyl group, a methoxy group or an identical or different aryl group or a heteroaryl group,
  an arylmethyl group, an aryl group of said arylmethyl group being optionally substituted with one to three groups, or
  a methylheteroaryl group,
$R^3$ is
  absent when B is O or S, or is
  H or a $(C_1-C_4)$alkyl group when B is N,
$R^4$ is a $(C_1-C_5)$alkyl group or a $(C_3-C_4)$cycloalkyl group, each group bearing a carboxylic acid group, and said $(C_1-C_5)$alkyl group or $(C_3-C_4)$cycloalkyl group being optionally substituted by a hydroxyl group, a halogen group or a methoxy group, and
when B is N, $R^3$ and $R^4$ can together form a 5- or 6-membered heterocycle substituted by a carboxylic acid group, and optionally substituted by a halogen atom, a hydroxyl group, a methoxy group or a hydroxymethyl group, or alternatively substituted by an ethylic acid,
or pharmaceutically acceptable salts thereof,
wherein the disease characterized by a reduction in macrophage-mediated bacterial killing is selected from the group consisting of asthma, chronic obstructive pulmonary disease (COPD), cystic fibrosis, pneumonia, tuberculosis, and a disease involving pulmonary microbial infection selected from the group consisting of an infection by a bacterium from the genus *Haemophilus, Pseudomonas, Burkholderia, Staphylococcus, Mycobacterium, Prevotella, Veillonella, Propionibacterium, Actinomyces, Streptococcus*, and *Legionnella*.

2. The method according to claim 1, wherein the group NHR² of the compound of formula (I) is selected from the group consisting of:

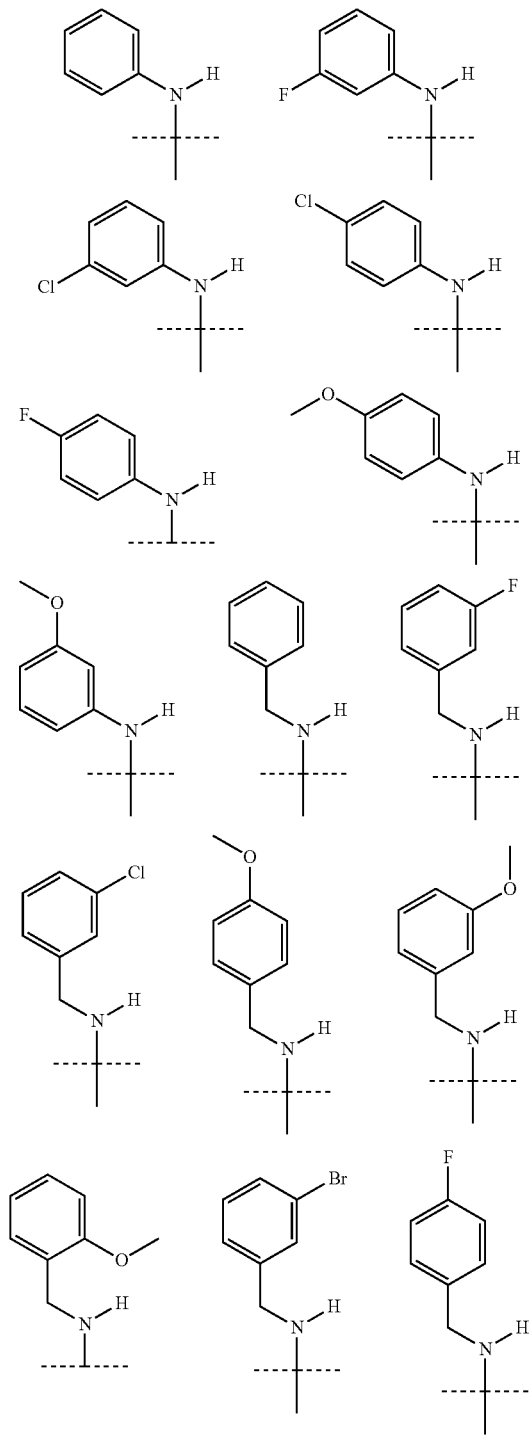

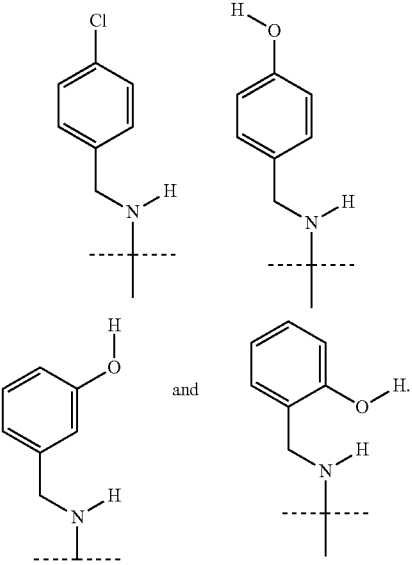

3. The method according to claim 1, wherein B is N and the group NR³R⁴ is selected from the group consisting of:

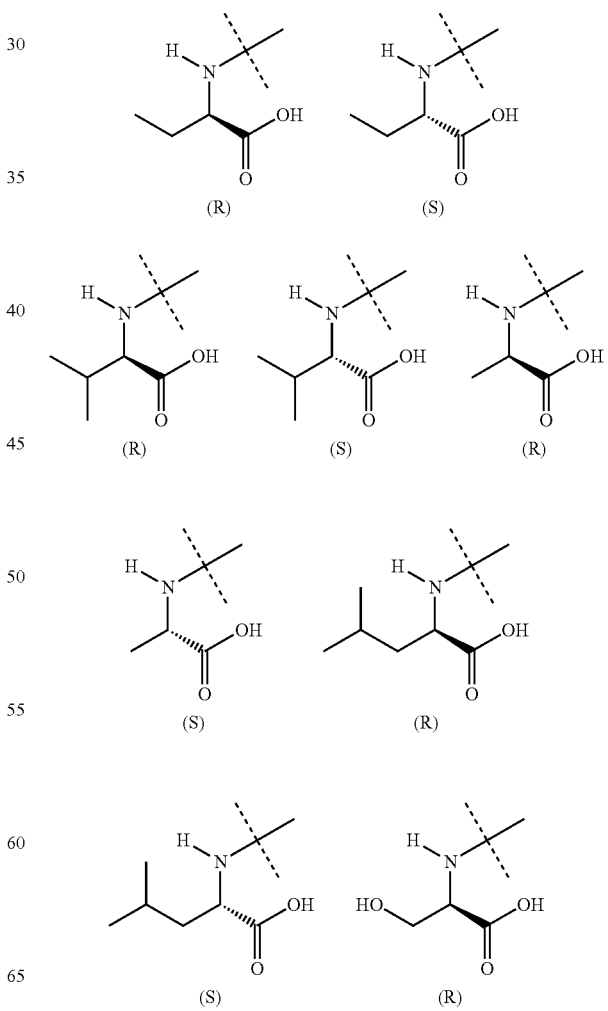

-continued

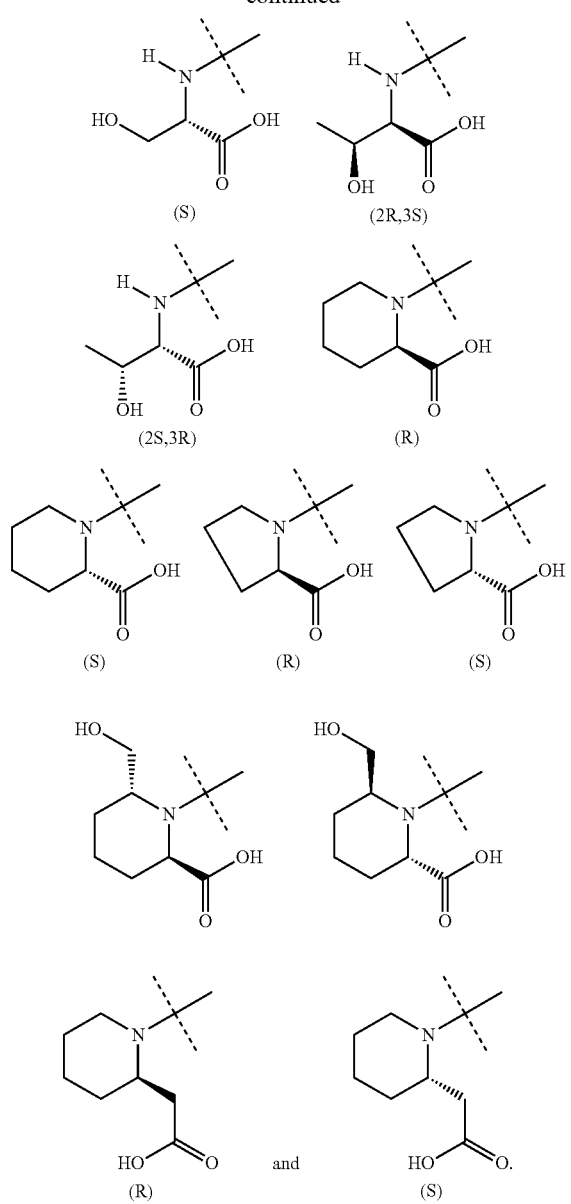

or alternatively B is O and OR⁴ is selected from the group consisting of:

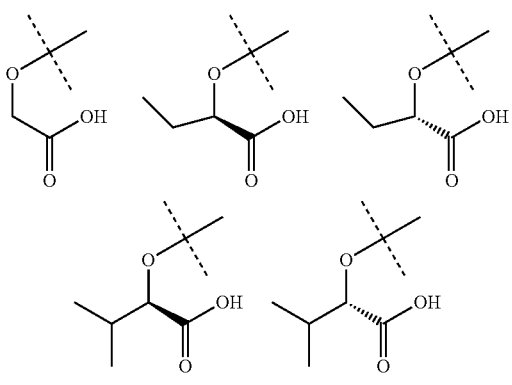

-continued

4. The method according to claim 1, wherein $R^1$ represents isopropyl, $R^2$ represents a benzyl group, $R^3$ represents a hydrogen atom and $R^4$ represents a 1-carboxypropan-1-yl group, in the (R) or (S) form or in the form of a racemic mixture thereof.

5. The method according to claim 1, wherein the compound of formula (I) is (2R)-2-[[9-isopropyl-6-(phenylmethylamino)purin-2-yl]amino]butanoic acid.

6. The method according to claim 1, wherein the disease characterized by a reduction in macrophage-mediated bacterial killing is a disease involving pulmonary microbial infection selected from the group consisting of an infection by a bacterium from the genus *Haemophilus, Pseudomonas, Burkholderia, Staphylococcus, Mycobacterium, Prevotella, Veillonella, Propionibacterium, Actinomyces, Streptococcus,* and *Legionnella*.

7. The method according to claim 1, wherein the disease characterized by a reduction in macrophage-mediated bacterial killing is cystic fibrosis.

8. The method according to claim 1, wherein the compound of formula (I) is orally administered in an amount of about 1 to 500 mg.

9. The method according to claim 1, wherein administration of a compound of formula (I) is administered by aerosol, in an amount from about 1 to about 100 mg per inhalation.

10. A compound selected from the group consisting of (3R)-3-[[6-(benzylamino)-9-isopropyl-purin-2-yl]amino] butanoic acid and (2S)-2-[[6-(benzylamino)-9-isopropyl-purin-2-yl]amino]-3-hydroxy-propanoic acid.

11. The method according to claim 1, comprising administration to the patient in need thereof the compound of formula (I) in the form of a pharmaceutical composition also comprising a pharmaceutically acceptable carrier.

12. The method according to claim 11, wherein the pharmaceutical composition is administered by oral, systemic, parenteral, or intra-pulmonary administration.

13. The method according to claim 11, wherein the pharmaceutical composition further comprises an additional agent selected from the group consisting of mucolytic agent, bronchodilator, an anti-inflammatory agent, and an anti-infective agent.

14. A method for identifying a patient with an increased likelihood of responding to a compound of formula (I), wherein the patient has been diagnosed with or is at increased risk of developing a pulmonary disease, said method comprising:
a) providing isolated macrophages from said individual;
b) incubating said macrophages with a microorganism able to provoke a pulmonary disease;
c) providing to said macrophages an effective amount of the compound of formula (I); and
d) assessing the abilities of said macrophages to kill said microorganism, wherein the compound of formula (I) is:

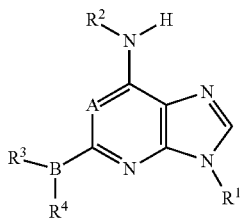

or pharmaceutically acceptable salts thereof
wherein
A is N or CH,
B is N, O, or S,
$R^1$ is
  H,
  a $(C_1-C_4)$alkyl group,
  a methyl$(C_3-C_6)$cycloalkyl group, or
  a $(C_3-C_6)$cycloalkyl group,
$R^2$ is
  an aryl, said aryl group being optionally substituted by an halogen atom, an hydroxyl group, a methoxy group or an identical or different aryl group or a heteroaryl group,
  an arylmethyl group, an aryl group of said arylmethyl group being optionally substituted with one to three groups, or
  a methylheteroaryl group,
$R^3$ is
  absent when B is O or S, or is
  H or a $(C_1-C_4)$alkyl group when B is N,
$R^4$ is a $(C_1-C_5)$alkyl group or a $(C_3-C_4)$cycloalkyl group, each group bearing a carboxylic acid group, and said $(C_1-C_5)$alkyl group or $(C_3-C_4)$cycloalkyl group being optionally substituted by a hydroxyl group, a halogen group or a methoxy group, and
when B is N, $R^3$ and $R^4$ can together form a 5- or 6-membered heterocycle substituted by a carboxylic acid group, and optionally substituted by a halogen atom, a hydroxyl group, a methoxy group or a hydroxymethyl group, or alternatively substituted by an ethylic acid or pharmaceutically acceptable salts thereof.

15. The method according to claim 1, wherein the disease involving pulmonary microbial infection is selected from the group consisting of an infection by *Pseudomonas aeruginosa, Staphylococcus aureus, Burkholderia cepacia, Haemophilus influenza, Mycobacterium absessus,* and *Mycobacterium tuberculosis.*

16. The method according to claim 1, wherein the group that substitutes the benzyl of $R^2$ is selected from the group consisting of a $(C_1-C_3)$alkyl group, a OH, a OMe, or a halogen group.

17. The method according to claim 12, wherein the intra-pulmonary administration consists of an intra-bronchial or an intra-alveolar administration.

18. The method according to claim 13, wherein the anti-infective agent is selected from the group consisting of an antibiotic and a bacteriophage.

19. The method according to claim 1, wherein the group that substitutes the aryl group of the arylmethyl group of $R^2$ is selected from the group consisting of a $(C_1-C_3)$alkyl group, a OH, a OMe, or a halogen group.

20. The method according to claim 14, wherein the group that substitutes the aryl group of the arylmethyl group of $R^2$ is selected from the group consisting of a $(C_1-C_3)$alkyl group, a OH, a OMe, or a halogen group.

* * * * *